United States Patent

Kollmeyer et al.

Patent Number: 4,525,201
Date of Patent: Jun. 25, 1985

[54] OXASPIRO ALKANE AND ALKENE ETHER HERBICIDES

[75] Inventors: Willy D. Kollmeyer; Thomas L. Brown, both of Modesto, Calif.

[73] Assignee: Shell Oil Company, Houston, Tex.

[21] Appl. No.: 544,762

[22] Filed: Oct. 24, 1983

[51] Int. Cl.³ .................... A01N 43/08; A01N 43/40; C07D 213/06; C07D 307/04

[52] U.S. Cl. ............................ 71/76; 71/88; 71/92; 71/93; 71/94; 544/230; 546/15; 549/331; 549/332; 549/333; 549/341

[58] Field of Search ............... 549/331, 332, 333, 341; 546/15; 544/230; 71/88, 76

[56] References Cited

U.S. PATENT DOCUMENTS

| Re. 30,574 | 4/1981 | Barker et al. | 71/88 |
|---|---|---|---|
| 3,919,252 | 11/1975 | Barker et al. | 549/341 |
| 4,116,669 | 9/1978 | Barker et al. | 71/88 |
| 4,255,587 | 3/1981 | Plath et al. | 71/88 |
| 4,261,733 | 4/1981 | Chupp | 71/88 |
| 4,282,388 | 8/1981 | Draber et al. | 568/660 |
| 4,289,884 | 9/1981 | Barker | 546/283 |
| 4,400,198 | 8/1983 | Orr et al. | 71/88 |
| 4,407,670 | 10/1983 | Crabb et al. | 71/88 |
| 4,410,354 | 10/1983 | Sundelin et al. | 71/94 |

*Primary Examiner*—Glennon H. Hollrah
*Assistant Examiner*—Andrew Duff Meikle

[57] ABSTRACT

The present invention is directed to novel compounds of formulas I or II

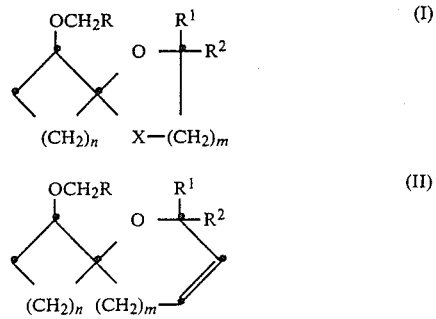

wherein R is an optionally substituted unsaturated group containing up to 4 carbon atoms, a cycloalkyl group containing 3 to 10 carbon atoms, a secondary alkyl group containing 3 to 10 carbon atoms, an aromatic group containing up to 14 carbon atoms or a heterocyclic group containing up to 14 carbon atoms; in formula I, m is 0, 1 or 2; n is 1, 2 or 3; $R^1$ and $R^2$ each independently is a hydrogen atom, an alkyl group containing 1 to 6 carbon atoms, or a hydroxyalkyl or an alkoxymethyl group in which the alkyl portion contains 1 to 6 carbon atoms; X is $CH_2$ when m is 0, 1 or 2; or X is oxygen when m is 1 or 2; or in formula II, n is 1, 2 or 3; m is 0 or 1; and $R^1$ and $R^2$ each independently is a hydrogen atom, an alkyl group containing 1 to 6 carbon atoms, or a hydroxyalkyl or an alkoxymethyl group in which the alkyl portion contains 1 to 6 carbon atoms. The compounds of formulas I and II are useful as plant growth regulators or herbicides.

11 Claims, No Drawings

OXASPIRO ALKANE AND ALKENE ETHER HERBICIDES

BACKGROUND OF THE INVENTION

1. Field of the Invention

The present invention is directed to new oxaspiroalkane ethers, their use as herbicides and to compositions thereof.

2. Summary of the Invention

The present invention is directed to novel compounds of formulas I or II

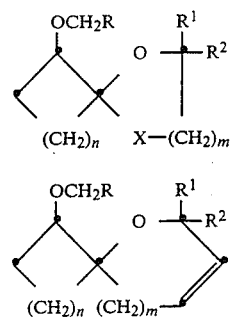

wherein R is an optionally substituted unsaturated group containing up to 4 carbon atoms, a cycloalkyl group containing 3 to 10 carbon atoms, a secondary alkyl group containing 3 to 10 carbon atoms, an aromatic group containing up to 14 carbon atoms or a heterocyclic group containing up to 14 carbon atoms; in formula I, m is 0, 1 or 2; n is 1, 2 or 3; $R^1$ and $R^2$ each independently is a hydrogen atom, an alkyl group containing 1 to 6 carbon atoms, or a hydroxyalkyl or an alkoxymethyl group in which the alkyl portion contains 1 to 6 carbon atoms; X is $CH_2$ when m is 0, 1 or 2 or X is oxygen when m is 1 or 2; or in formula II, n is 1, 2 or 3; m is 0 or 1; and $R^1$ and $R^2$ each independently is a hydrogen atom, an alkyl group containing 1 to 6 carbon atoms, or a hydroxyalkyl or an alkoxymethyl group in which the alkyl portion contains 1 to 6 carbon atoms. The compounds of formulas I and II are useful as plant growth regulators or herbicides.

In the compounds of formulas I or II, preferably $R^1$ and $R^2$ each independently is a hydrogen atom or a methyl or ethyl group. In one embodiment of the invention, $R^1$ and $R^2$ each is methyl group. Illustrative examples of such compounds include those species having the following structural features in formula I

| m | n | X | $R^1$ | $R^2$ | R |
|---|---|---|---|---|---|
| 1 | 3 | $CH_2$ | $CH_3$ | $CH_3$ | 2-chlorophenyl |
| 1 | 3 | $CH_2$ | $CH_3$ | $CH_3$ | 2-methylphenyl |
| 1 | 3 | $CH_2$ | $CH_3$ | $CH_3$ | 2-pyridinyl |
| 2 | 2 | $CH_2$ | $CH_3$ | $CH_3$ | 2-fluorophenyl |
| 2 | 2 | $CH_2$ | $CH_3$ | $CH_3$ | 2-chlorophenyl |
| 2 | 2 | $CH_2$ | $CH_3$ | $CH_3$ | 2-methylphenyl |
| 2 | 2 | $CH_2$ | $CH_3$ | $CH_3$ | 2-pyridinyl |
| 2 | 1 | 0 | $CH_3$ | $CH_3$ | 2-fluorophenyl |
| 2 | 1 | 0 | $CH_3$ | $CH_3$ | 2-chlorophenyl |
| 2 | 1 | 0 | $CH_3$ | $CH_3$ | 2-methylphenyl |
| 2 | 1 | 0 | $CH_3$ | $CH_3$ | 2-pyridinyl |

In the compounds of formulas I or II, preferably R is an ethynyl group, a 2-pyridinyl group or a phenyl group optionally substituted by 1 or 2 chlorine or fluorine atoms or methyl group. In specific embodiments of the invention, R is a 2-chlorophenyl, a 2-fluorophenyl or a 2-methylphenyl group.

In the compounds of formula I, preferably m is 1 and n is 1 or 2, and for compounds of formula II, preferably m is 0 and n is 1 or 2. Illustrative examples of such compounds include those species having the following structural features

| Formula I | | | | | |
|---|---|---|---|---|---|
| m | n | X | $R^1$ | $R^2$ | R |
| 1 | 2 | 0 | H | H | 2-chlorophenyl |
| 1 | 2 | 0 | H | H | 2-methylphenyl |
| 1 | 2 | 0 | H | H | 2-pyridinyl |
| 1 | 2 | $CH_2$ | H | H | 2-chlorophenyl |
| 1 | 2 | $CH_2$ | H | H | 2-methylphenyl |
| 1 | 2 | $CH_2$ | H | H | 2-pyridinyl |
| 1 | 2 | $CH_2$ | $CH_3$ | $CH_3$ | 2-chlorophenyl |
| 1 | 2 | $CH_2$ | $CH_3$ | $CH_3$ | 2-methylphenyl |
| 1 | 2 | $CH_2$ | $CH_3$ | $CH_3$ | 2-pyridinyl |
| 1 | 1 | 0 | H | H | 2-chlorophenyl |
| 1 | 1 | 0 | H | H | 2-methylphenyl |
| 1 | 1 | 0 | H | H | 2-pyridinyl |
| 1 | 1 | $CH_2$ | H | H | 2-chlorophenyl |
| 1 | 1 | $CH_2$ | H | H | 2-methylphenyl |
| 1 | 1 | $CH_2$ | H | H | 2-pyridinyl |
| 1 | 1 | 0 | $CH_3$ | $CH_3$ | 2-chlorophenyl |
| 1 | 1 | 0 | $CH_3$ | $CH_3$ | 2-pyridinyl |

| Formula II | | | | | |
|---|---|---|---|---|---|
| m | n | X | $R^1$ | $R^2$ | R |
| 0 | 2 | — | $CH_3$ | $CH_3$ | 2-chlorophenyl |
| 0 | 2 | — | $CH_3$ | $CH_3$ | 2-methylphenyl |
| 0 | 2 | — | $CH_3$ | $CH_3$ | 2-pyridinyl |

In the compounds of formula I, X is preferably $CH_2$.

The compounds of formulas I and II of the present invention can exist in several stereoisomeric forms, such as cis-configuration, trans-configuration, as well as in optically-active forms. These individual forms as well as mixtures thereof are within the scope of the compounds of formulas I and II of the present invention. The various isomers of the compounds of the invention may have different herbicidal or plant growth regulator properties and usually the compounds having the cis-configuration of the ether substituent to the oxygen atom of the heterocyclic ring have the highest biological activity. One may prefer to deliberately create mixtures or to resolve an isomer mixture to recover a more active isomer form or to prepare the more active form directly for use in the invention. The compounds of the invention also have utility as solvents or dispersing agents for pigments, paints, polymers and synthetic fibers.

Illustrative embodiments of the compounds of formula I of the invention include those species having the following structural features

| m | n | X | $R^1$ | $R^2$ | R |
|---|---|---|---|---|---|
| 1 | 3 | 0 | H | H | 2-chlorophenyl |
| 1 | 3 | 0 | H | H | 2-methylphenyl |
| 1 | 3 | 0 | H | H | 2-pyridinyl |
| 1 | 3 | $CH_2$ | H | H | 2-chlorophenyl |
| 1 | 3 | $CH_2$ | H | H | 2-methylphenyl |
| 1 | 3 | $CH_2$ | H | H | 2,6-dichlorophenyl |
| 1 | 3 | $CH_2$ | H | H | 2-pyridinyl |
| 1 | 3 | $CH_2$ | H | H | 2-ethynyl |
| 1 | 3 | $CH_2$ | H | H | 2-pyrimidinyl |
| 1 | 3 | $CH_2$ | H | H | 4,6-dimethyl-1,3,5-triazin-2-yl |

-continued

| m | n | X | R¹ | R² | R |
|---|---|---|---|---|---|
| 1 | 3 | CH₂ | H | H | cyclopropyl |
| 1 | 3 | CH₂ | H | H | tetrahydro-2-pyranyl |
| 2 | 3 | O | H | H | 2-fluorophenyl |
| 2 | 3 | O | H | H | 2-chlorophenyl |
| 2 | 3 | O | H | H | 2-methylphenyl |
| 2 | 3 | O | H | H | 2-pyridinyl |
| 2 | 3 | CH₂ | H | H | 2-fluorophenyl |
| 2 | 3 | CH₂ | H | H | 2-chlorophenyl |
| 2 | 3 | CH₂ | H | H | 2-methylphenyl |
| 2 | 3 | CH₂ | H | H | 2-pyridinyl |
| 2 | 3 | CH₂ | CH₃ | CH₃ | 2-fluorophenyl |
| 2 | 3 | CH₂ | CH₃ | CH₃ | 2-chlorophenyl |
| 2 | 3 | CH₂ | CH₃ | CH₃ | 2-methylphenyl |
| 2 | 3 | CH₂ | CH₃ | CH₃ | 2-pyridinyl |
| 2 | 2 | O | H | H | 2-fluorophenyl |
| 2 | 2 | O | H | H | 2-chlorophenyl |
| 2 | 2 | O | H | H | 2-methylphenyl |
| 2 | 2 | O | H | H | 2-pyridinyl |
| 2 | 2 | CH₂ | H | H | 2-fluorophenyl |
| 2 | 2 | CH₂ | H | H | 2-chlorophenyl |
| 2 | 2 | CH₂ | H | H | 2-methylphenyl |
| 2 | 2 | CH₂ | H | H | 2-pyridinyl |
| 2 | 1 | O | H | H | 2-fluorophenyl |
| 2 | 1 | O | H | H | 2-chlorophenyl |
| 2 | 1 | O | H | H | 2-methylphenyl |
| 2 | 1 | O | H | H | 2-pyridinyl |
| 2 | 1 | CH₂ | H | H | 2-fluorophenyl |
| 2 | 1 | CH₂ | H | H | 2-chlorophenyl |
| 2 | 1 | CH₂ | H | H | 2-methylphenyl |
| 2 | 1 | CH₂ | H | H | 2-pyridinyl |

The compounds of formula I of the invention wherein m is 0, 1 or 2 and X is CH₂ are prepared from 2-RCH₂O-ether-substituted cycloalkanols III

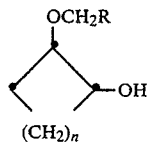

III in which n is 1, 2 or 3 and R is an optionally substituted unsaturated group containing up to 4 carbon atoms, a cycloalkyl group containing 3 to 10 carbon atoms, a secondary alkyl group containing 3 to 10 carbon atoms, an aromatic group containing up to 14 carbon atoms or a heterocyclic group containing up to 14 carbon atoms, by oxidation to the corresponding ketone, reaction with the appropriate Grignard reagent to form the corresponding vinylic, allylic or homoallylic cyclohexanol ether followed by spirocyclization.

The oxidation of the substituted cycloalkanols is conducted by conventional techniques known in the art, for example, using (a) potassium dichromate in (sulfuric) acid in the presence of tetrabutylammonium bisulfate and methylene chloride, or (b) (COCl)₂, dimethyl sulfoxide and triethylamine in methylene chloride as taught by Swern et al, *J. Org. Chem.*, 1978, 43(12), page 2480.

The ketone from the above oxidation was treated with the appropriate conventional Grignard reagent system to form the desired vinylic, allylic or homoallylic substituted cycloalkanol in the presence of anhydrous ethers, such as tetrahydrofuran, as taught by Still and McDonald, *Tetrahedron Letters*, 1980, 21, page 1031.

The vinylic, allylic or homoallylic substituted cycloalkanols are spirocyclized by application of conventional techniques known in the art, for example, (a) formation of a 1,3-, 1,4- or 1,5-diol, e.g. with diborane-tetrahydrofuran, sodium hydroxide and hydrogen peroxide followed by treatment with triphenylphosphine and diethyl diazoacetate; and the allylic or homoallylic substituted cycloalkanols are also spirocyclized by (b) acid catalyzed cyclization of a, 4- or 5-alken-1-ol, e.g. with aqueous p-toluenesulfonic acid in benzene at room temperature of (c) epoxidation-cyclization of a, 4- or 5-alken-1-ol, e.g. with m-chloroperbenzoic acid in methylene chloride.

The compounds of formula I of the invention wherein m is 1 or 2 and X is O are prepared from the ether-substituted cycloalkanols, III, by oxidation to the corresponding ketone as described above followed by treating the resulting ketone with the appropriate diol, e.g. ethylene glycol and a catalyst such as p-toluenesulfonic acid or the like.

The compounds of formula II of the invention are prepared by conventional techniques from the ether substituted cycloalkanols of formula III by first preparing the corresponding ketone as described above and by treating the ketone with a 3,3-dialkyl-3-(dimethyl-t-butylsilyloxy)propyne or butyne compound and an appropriate Grignard reagent system, e.g. alkylmagnesium chloride in tetrahydrofuran, hydrogenating the resulting product, e.g. with palladium on barium sulfate and quinoline, and cyclizing the resulting product, e.g. with tetraalkylammonium fluoride in tetrahydrofuran followed by aqueous p-toluenesulfonic acid in benzene, to give the desired compound of formula II.

The ether-substituted cycloalkanols of formula III are prepared by treating cycloalkanediols with a compound of the formula RCH₂X in which R is defined as in formula I or II above and X is a halogen atom, such as bromine, chlorine or iodine, or is a mesyloxy, tosyloxy group or the like, in the presence of a base and an inert diluent. The base is suitably an alkali metal hydride, hydroxide or carbonate, including, for example, sodium hydride, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. The reaction can be conducted in a two-phase system, preferably in the presence of a phase-transfer catalyst. For example, the system is aqueous sodium or potassium hydroxide solution with toluene or methylene chloride and the phase-transfer catalyst is an ammonium compound such as tetra-n-butylammonium chloride, bromide, or hydrogen sulfate, triethylbenzylammonium chloride or the like. The reaction is usually carried out under normal pressures and ambient temperatures. Suitable temperatures for the reaction are from about 0° to about 120° C., preferably from about 20° to about 100° C. The product ethers are recovered and isolated by conventional techniques. The cycloalkanediols, some of their ethers and their preparations are known as, for example, in U.S. Pat. No. 4,282,388.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

Embodiment 1—2-(2-Fluorobenzyloxy)cyclohexanol

A 200 ml round bottom flask was dried and cooled under nitrogen. The flask was charged with 70 ml of dry 1,2-dimethoxyethane, 30 g of 1,2-cyclohexanediol, 37.3 g of 2-fluorobenzyl chloride, 10.4 g of flaked sodium hydroxide and 1 g of Aliquat 336 (benzyltricaprylylammonium chloride). The stirred reaction mixture was heated to 95° C. over one-half hour and then at 95°-110° C. for one and one-half hours. A total of 45 ml of solvent was collected in a Dean-Stark trap over two hours. The reaction mixture was cooled to room temperature, poured into 600 ml of water, the resulting aqueous phase was extracted three times with 100 ml of methylene chloride, the combined extracts were washed successively with 500 ml of 1% hydrochloric acid solution and 500 ml of saturated sodium chloride solution, dried ($MgSO_4$) and concentrated under vacuum to give 50.2 g of a yellow oil, which upon Kugelrohr distillation yielded 38.9 g of the desired product, b.p. 90° C. (0.02 mm).

Embodiment 2—2-(2-Fluorobenzyloxy)cyclohexanone

A solution of 5.0 g of 2-(2-fluorobenzyloxy)cyclohexanol dissolved in 60 ml of methylene chloride and a solution of 2.7 g of potassium dichromate in 60 ml of 9M sulfuric acid were placed in a 250 ml separatory funnel followed by 0.7 g of tetrabutylammonium bisulfate. The reaction mixture was shaken vigorously and an exothermic reaction followed. After three minutes, no alcohol reactant was present. The phases were separated, the aqueous phase was extracted twice with 30 ml of methylene chloride, the combined organic layers were washed with 400 ml of water, dried ($MgSO_4$) and stripped to give 4.15 g of a yellow oil, which was chromatographed over silica using a 40:8:2 hexane:ethyl acetate:tetrahydrofuran mixture as eluent to yield 3.0 g of the desired product as a colorless liquid.

Embodiment 3—2-(2-Fluorobenzyloxy)cyclohexanone Ethylene Ketal

To a solution of 2.0 g of 2-(2-fluorobenzyloxy)cyclohexanone in 100 ml of benzene was added 5.6 g of ethylene glycol followed by 0.25 g of p-toluenesulfonic acid. The reaction mixture was heated at reflux for three hours until water evolution ceased. After cooling, 3.0 g of solid potassium carbonate was added and the reaction mixture was poured into 200 ml of 10% potassium cabonate solution, extracted three times with 40 ml of methylene chloride, dried and stripped to give 2.40 g of the desired product as a nearly colorless oil.

Embodiment 4—2-(2-Fluorobenzyloxy)cyclopentanol

Following procedures similar to those described in Embodiment 1 above, the desired product was prepared, b.p. 97° C. (0.015 mm), from 1,2-cyclopentanediol (Embodiment 27).

Embodiment 5—2-(2-Fluorobenzyloxy)cyclopentanone

The desired product was prepared from 2-(2-fluorobenzyloxy)cyclopentanol following procedures similar to those described in Embodiment 2 above.

Embodiment 6—2-(2-Fluorobenzyloxy)cyclopentanone Ethylene Ketal

The desired product was prepared from 2-(2-fluorobenzyloxy)cyclopentanone following procedures similar to those in Embodiment 3 above.

Embodiment 7—cis-2-(2-Fluorobenzyloxy)cyclobutanol

The desired product was prepared from cis-1,2-cyclobutanediol (as in Embodiment 33) following procedures similar to those described in Embodiment 1 using chromatographic separation with 1:1 diethyl ether:hexanes as eluent.

Embodiment 8—2-(2-Fluorobenzyloxy)cyclobutanone

A dry 300 ml round bottom flask was purged with argon and charged with 125 ml of dry methylene chloride followed by injection of 7.84 g of $(COCl)_2$ by syringe. The solution was cooled to −65° C. and 10.52 g of dimethyl sulfoxide was added dropwise with vigorous stirring and with vigorous evolution of gas. After the addition was complete, the solution was stirred at −65° C.±1° C. over 30 minutes and then 11.0 g of 2-(2-fluorobenzyloxy)cyclobutanol dissolved in 25 ml of dry methylene chloride was added over 20 minutes. After this addition was complete, the mixture was stirred at −65° C. for 40 minutes, then 28.4 g of triethylamine was added dropwise at −65° C. and the reaction mixture was allowed to warm to ambient temperatures. The reaction mixture was poured into 250 ml of water and extracted three times with 100 ml of methylene chloride, the combined extracts were washed with 150 ml of water, dried ($MgSO_4$) and stripped to give 11.3 g of brown oil. The crude product was chromatographed over 500 g of silica and eluted with 35% diethyl ether in hexane to give 10.0 g of the desired product.

Embodiment 9—2-(2-Fluorobenzyloxy)cyclobutanone Ethylene Ketal

The desired product was prepared from 2-(2-fluorobenzyloxy)cyclobutanone following procedures similar to those described in Embodiment 3 above.

Embodiment 10—2-(2-Fluorobenzyloxy)-1-(2-propenyl)cyclohexanol

A dry 100 ml round bottom flask fitted with a nitrogen inlet, dropping funnel and stirrer, was charged with 10 ml of dry tetrahydrofuran and 12 ml of allylmagnesium chloride. With cooling to 0° C., 4.0 g of 2-(2-fluorobenzyloxy)cyclohexanone (Embodiment 2 above) in 10 ml of tetrahydrofuran was added dropwise over 20 minutes. After stirring an additional 20 minutes at 0° C., the reaction mixture was quenched with 10 ml of saturated ammonium chloride solution, poured into 100 ml of water, and extracted with five 30 ml portions of diethyl ether. The extract was dried and stripped to give 4.8 g of the desired product as a colorless oil.

Embodiment 11—2-(2-Fluorobenzyloxy)-1-(3-hydroxypropyl)cyclohexanol

A dry 100 ml flask was purged with argon and charged with 20 ml of dry tetrahydrofuran and 18.9 ml of 1M diborane-tetrahydrofuran. The solution was cooled at −3° C. and 2.5 g of 2-(2-fluorobenzyloxy)-1-(2-propenyl)cyclohexanol (Embodiment 10 above) was added dropwise over five minutes. The reaction mixture was allowed to stand at −5° C. for one hour and then at room temperature for two hours. Then 10 ml of water was added dropwise over 10 minutes followed by 6 ml of 5N sodium hydroxide and finally 3.5 ml of 30% hydrogen peroxide. After phase separation, the organic layer was washed with 15 ml of water, two 50 ml portions of saturated sodium chloride solution, dried (MgSO$_4$) and stripped to give 2.61 g of the desired product.

Embodiment 12—6-(2-Fluorobenzyloxy)-1-oxaspiro[4.5]decane

A dry 50 ml round bottom flask under nitrogen was charged with 25 ml of dry methylene chloride, 2.43 g of triphenylphosphine and 2.61 g of 2-(2-fluorobenzyloxy)-1-(3-hydroxypropyl)cyclohexanol. The reaction mixture was cooled at 5° C. and 2.15 g of diethyl azodicarboxylate in 3 ml of methylene chloride was added dropwise with stirring. The temperature of the reaction mixture, which rose to 10° C. during the addition, was kept for 15 minutes at 5° C., then allowed to warm to room temperature overnight. The reaction mixture was diluted with 30 ml of methylene chloride and poured into 50 ml of water. After extraction with 30 ml of methylene chloride, the combined organic phases were dried and stripped. The resulting oil was stirred vigorously with three 25 ml portions of hexane and the hexane extract concentrated to give 2.8 g of a yellow oil, which was chromatographed over 150 g of silica to give 0.8 g of the desired product.

Embodiment 13—2-(2-Fluorobenzyloxy)-1-(2-propenyl)cyclopentanol

The desired product was prepared from 2-(2-fluorobenzyloxy)cyclopentanone at −78° C. using procedures similar to those described in Embodiment 10 above.

Embodiment 14—2-(2-Fluorobenzyloxy)-1-(3-hydroxypropyl)cyclopentanol

The desired product was prepared from 2-(2-fluorobenzyloxy)-1-(2-propenyl)cyclopentanol by procedures similar to those described in Embodiment 11 above.

Embodiment 15—6-(2-Fluorobenzyloxy)-1-oxaspiro[4.4]nonane

A dry 50 ml roundbottom flask was charged with 20 ml of dry pyridine under nitrogen. Then 1.7 g of 2-(2-fluorobenzyloxy)-1-(3-hydroxypropyl)cyclopentanol was added followed by 1.12 g of benzenesulfonyl chloride. After the addition was complete the solution was stirred at room temperature overnight. The reaction mixture was poured into water and extracted three times with 40 ml of diethyl ether. The extract was dried and stripped to give 1.1 g of yellow oil, which was chromatographed on 75 g of silica using 1:4:20 solution of tetrahydrofuran:ethyl acetate:hexane as eluent to yield 0.8 g of the desired product.

Embodiment 16—2-cis-(2-Fluorobenzyloxy)-1-(2-propenyl)cyclobutanol

The desired product was prepared from 2-(2-fluorobenzyloxy)cyclobutanone following procedures similar to those described in Embodiment 10 above.

Embodiment 17—2-(2-Fluorobenzyloxy)-1-(3-hydroxypropyl)cyclobutanol

The desired product was prepared from 2-(2-fluorobenzyloxy)-1-(2-propenyl)cyclobutanol following procedures similar to those described in Embodiment 11 above.

Embodiment 18—1-(2-Fluorobenzyloxy)-5-oxaspiro[3.4]octane, cis-isomer

The desired product was prepared from 2-cis-(2-fluorobenzyloxy)-1-(3-hydroxyprop-1-yl)cyclobutanol following procedures similar to those described in Embodiment 12 above.

Embodiment 19—2-(2-Fluorobenzyloxy)-1-(3-ethyl-3-butenyl)cyclohexanol

A 100 ml flask was dried under argon and charged with 0.82 g of magnesium and 50 ml of dry tetrahydrofuran. To this mixture, was added a few crystals of iodine followed by 0.1 ml of 1,2-dibromoethane. After ethylene evolution had nearly ceased, 4.1 g of a 70% tetrahydrofuran solution of 2,2-bis-(chloromethyl)-1-chlorobutane was added dropwise to maintain gentle reflux. The resulting solution was held at reflux for 15 minutes, and then stirred at room temperature for one-half hour. Then 3.0 g of 2-(2-fluorobenzyloxy)cyclohexanone (Embodiment 2) in 5 ml of tetrahydrofuran was added dropwise. The mixture was stirred at room temperature for one hour, quenched with 10 ml of saturated ammonium chloride solution, poured into 100 ml of water, and extracted three times with 75 ml portions of methylene chloride. The extract was dried and stripped to give 2.9 g of a yellow oil, which was chromatographed on 250 g of silica using a 30% diethyl ether in hexane eluent to give 1.2 g of the desired product as a colorless oil.

Embodiment 20—6-(2-Fluorobenzyloxy)-2-(hydroxymethyl)-2-ethyl-1-oxaspiro-[4.5]decane A 25 ml roundbottom flask was charged with 15 ml of methylene chloride and 0.4 g of 2-(2-fluorobenzyloxy)-1-(3-ethyl-3-butenyl)cyclohexanol (Embodiment 19) followed by 0.32 g of 85% m-chloroperbenzoic acid while stirring. The reaction mixture was stirred overnight, then poured into 40 ml of 5% sodium bicarbonate and extracted three times with 30 ml portions of methylene chloride. The extract was dried (MgSO$_4$) and stripped to give 0.42 g of a light yellow oil, which was chromatographed over 100 g of silica using a 40% solution of diethyl ether in hexane as eluent to yield 320 mg of the desired product as a mixture of diastereoisomers.

Embodiment 21—6-(2-Fluorobenzyloxy)-2-(methoxymethyl)-2-ethyl-1-oxaspiro[4.5]decane A dry 15 ml roundbottom flask under argon was charged with 5 ml of dry dimethylformamide and 100 mg of 6-(2-fluorobenzyloxy)-2-(hydroxymethyl)-2-ethyl-1-oxaspiro[4.5]decane (Embodiment 20) followed by 21 mg of 60% sodium hydride in mineral oil. The mixture was stirred at room temperature for two hours, warmed to 40° C. for three minutes, cooled to room temperature and then treated with 0.5 ml of methyl iodide in one portion to produce a white precipitate. After stirring overnight, the reaction mixture was quenched with a little water, poured into 50 ml of water, and extracted with three 25 ml portions of diethyl ether. The combined organic phases were washed twice with 25 ml portions of water, with 25 ml of sodium chloride solution, dried and stripped to give a crude product, which was chromatographed over 100 g of silica and eluted with hexane followed by a 20% solution of diethyl ether in hexane to give 90 mg of the desired product.

Embodiment 22—6-(2-Fluorobenzyloxy)-2,2-dimethyl-1-oxaspiro[4.5]decane

A 50 ml roundbottom flask was charged with 25 ml of benzene and 2.0 g of 2-(2-fluorobenzyloxy)-1-(3-methyl-3-butenyl)cyclohexanol (Embodiment 24) followed by 50 mg of p-toluenesulfonic acid monohydrate. The resulting solution was stirred at room temperature overnight, poured into 100 ml of 5% aqueous sodium bicarbonate, and extracted three times with 50 ml portions of diethyl ether. The combined organic phases were dried (MgSO$_4$) and stripped to give a light yellow oil, which was chromatographed over 175 g of silica using a 10% solution of diethyl ether in hexane to yield 1.4 g of the desired product as a colorless oil.

Embodiment 23—6-(2-Fluorobenzyloxy)-2-(hydroxymethyl)-2-methyl-1-oxaspiro-[4.5]decane A 50 ml roundbottom flask was charged with 25 ml of dry methylene chloride and 2-(2-fluorobenzyloxy)-1-(3-methyl-3-butenyl)cyclohexanol (Embodiment 24) followed by portionwise addition of 2.1 g of 85% m-chloroperbenzoic acid over 10 minutes while stirring. After standing at room temperature overnight, the reaction mixture was poured into 100 ml of 5% aqueous sodium bicarbonate and extracted three times with 50 ml portions of diethyl ether, dried and stripped to give 2.78 g of a light yellow oil, which was chromatographed over 200 g of silica using a 1:1 solution of diethyl ether:hexane to yield 0.9 g of the desired product.

Embodiment 24—2-(2-Fluorobenzyloxy)-1-(3-methyl-3-butenyl)cyclohexanol

The desired product was prepared from 2-(2-fluorobenzyloxy)cyclohexanone (Embodiment 2) and 2,2-bis(chloromethyl)-1-chloropropane following procedures similar to those described in Embodiment 19.

Embodiment 25—2-(2-Fluorobenzyloxy)-1-(3-methyl-3-butenyl)cyclopentanol

The desired product was prepared from 2-(2-fluorobenzyloxy)cyclopentanone (Embodiment 5) and 2,2-bis(chloromethyl)-1-chloropropane following procedures similar to those described in Embodiment 19.

Embodiment 26—2-(2-Fluorobenzyloxy)-1-(3-methyl-3-butenyl)cyclobutanol

The desired product was prepared from 2-(2-fluorobenzyloxy)cyclobutanone (Embodiment 8) and 2,2-bis(chloromethyl)-1-chloropropane following procedures similar to those described in Embodiment 19.

Embodiment 27—1,2-Cyclopentanediol

A two liter flask containing 800 ml of glacial acetic acid, 39 g of cyclopentene, 26.75 g of potassium iodate and 63.5 g of iodine was heated at 60°–70° C. for three hours. After cooling to 35° C., 49 g of potassium acetate was added. The solution was heated to reflux for four hours, allowed to stand at room temperature overnight, then stirred with 18 ml of water for one-half hour. Then the acetic acid was removed under vacuum, the residue was stirred vigorously with 500 ml of diethyl ether and filtered, and the ethereal filtrate was washed three times with 80 ml portions of saturated sodium thiosulfate solution, then with saturated sodium chloride solution, dried (MgSO$_4$) and stripped. The crude product was distilled to give a fraction with b.p. 82°–110° C. at 1.8 mm. This distillate was dissolved in 600 ml of methanol and 11.4 g of sodium methoxide was added. After one hour reflux, the solution was cooled to room temperature, $CO_2$ was bubbled through for one-half hour, the solution was diluted with 15 ml saturated sodium chloride and stirred vigorously with 500 ml of diethyl ether, filtered, dried (MgSO$_4$) and distilled to give 32.8 g of the desired product as a low melting solid.

Embodiment 28—2-(2-Fluorobenzyloxy)-1-(3-(tert-butyldimethylsilyloxy)-3,3-dimethylpropynyl)cyclopentanol A 100 ml roundbottom flask was dried under argon and charged with 40 ml of dry tetrahydrofuran and 6.9 ml of 2M ethylmagnesium chloride in tetrahydrofuran followed by dropwise addition of 2.72 g of 3-(tert-butyldimethylsilyloxy)-3,3-dimethylpropyne dissolved in 5 ml of tetrahydrofuran. The solution was stirred for one-half hour at room temperature and then heated to reflux for 20 minutes. After cooling to room temperature, 2.6 g of 2-(2-fluorobenzyloxy)cyclopentanone (Embodiment 5) dissolved in 10 ml of tetrahydrofuran was added dropwise, and the solution was stirred at room temperature for one hour, after which time it was deep red. The reaction mixture was quenched with saturated ammonium chloride, poured into 150 ml of water, and extracted three times with 50 ml portions of diethyl ether. The extract was dried and stripped to give 4.3 g of amber oil, which was chromatographed over 250 g of silica using a 25% solution of diethyl ether in hexane to give 2.5 g of the desired product as a mixture of stereoisomers.

Embodiment 29—6-(2-Fluorobenzyloxy)-2,2-dimethyl-1-oxaspiro[4.4]non-3-ene

A flask was charged with 2.34 g of 2-(2-fluorobenzyloxy)-1-(3-(tert-butyldimethylsilyloxy)-3,3-dimethylpropynyl)cyclopentanol (Embodiment 28), 125 ml of absolute ethanol, 0.3 g of 5% palladium on barium sulfate and 0.3 g of synthetic quinoline. The mixture was stirred and cooled to −8° C., the system purged with nitrogen and hydrogen was bubbled through the solution. After two hours the ice bath was allowed to melt. At 0° C. the catalyst turned from brown to black and gas chromatography showed reduction was taking place. After five hours, the system was purged with nitrogen, filtered, and stripped, and the crude product was chromatographed on silica using a 20% solution of diethyl ether in hexane to yield 1.4 g of a colorless oil. This oil was dissolved in 25 ml of dry tetrahydrofuran and 6.83 ml of 1M tetrabutylammonium fluoride was added at 3° C. After stirring for 45 minutes at room temperature, the reaction mixture was poured into 100 ml of 5% aqueous sodium bicarbonate and extracted three times with 50 ml portions of diethyl ether. The combined extracts were washed with sodium chloride, dried (MgSO$_4$), and stripped to give 1.2 g of light yellow oil. The oil was dissolved in 25 ml of benzene, 200 mg of p-toluenesulfonic acid. H$_2$O was added, and stirring was continued at room temperature for 24 hours. The reaction mixture was poured into 100 ml of 5% aqueous sodium bicarbonate and extracted three times with 25 ml of diethyl ether. The extract was washed with sodium chloride solution, dried (MgSO$_4$), and stripped to give 0.52 g of crude product, which was chromatographed over 100 g of silica using a 12% solution of diethyl ether in hexanes to give 0.50 g of the desired product as a mixture of isomers.

Embodiment 30—1-(2-Fluorobenzyloxy)-6,6-dimethyl-5-oxaspiro[3.4]octane, cis-isomer The desired product was prepared from 2-(2-fluorobenzyloxy)-1-(3-methyl-3-butenyl)cyclobutanol) (Embodiment 26) following procedures similar to those described in Embodiment 22.

Embodiment 31—1,2-Bis(trimethylsilyloxy)cyclobutene

A dry, argon-filled, 1000 ml flask equipped with a reflux condenser, argon bubbler, mechanical stirrer and dropping funnel was charged with 300 ml of dry toluene and 23.0 g of sodium spheres. The mixture was heated to reflux and stirred vigorously. After cooling to room temperature, 119.5 g of trimethylsilylchloride was added over 10 minutes followed by 43.6 g of diethyl succinate over 10 minutes. The mixture was heated to reflux for 17 hours, cooled to room temperature, and filtered through a celite bed. Solvent was evaporated from the filtrate and the product was distilled at 79° C. to give 34.5 g of the desired product as a colorless liquid.

Embodiment 32—cis-1,2-Bis(trimethylsilyloxy)cyclobutane

A one liter autoclave was purged with nitrogen and charged with 69.7 g of 1,2-bis(trimethylsilyloxy)cyclobutene (Embodiment 31) and 0.95 g of 10% palladium on carbon. The system was purged with hydrogen, pressurized to 1300 psig and warmed to 60°–70° C., with periodic repressurization to 1300 psig. After eighteen hours, the autoclave was cooled to room temperature. The reaction mixture was washed out of the autoclave with methylene chloride, filtered through celite, distilled to remove solvent at room temperature and fractionated at 13 mm to obtain the desired product as 57.9 g of the fraction boiling at 74°–80° C.

Embodiment 33—cis-1,2-Cyclobutanediol

A 43.5 g sample of cis-1,2-bis(trimethylsilyloxy)cyclobutane dissolved in 200 ml of 20% aqueous acetone was heated to reflux for nine hours, the solvent was distilled off, and the residue was taken up in 200 ml of chloroform, dried (MgSO$_4$), distilled at 52°–54° C. to give 12.9 g of the desired product as a colorless liquid.

Embodiment 34—6-(2-Fluorobenzyloxy)-2,2-dimethyl-1-oxaspiro[4.4]nonane

The desired product was prepared from 2-(2-fluorobenzyloxy)-1-(3-methyl-3-butenyl)cyclopentanol (Embodiment 25) following procedures similar to those described in Embodiment 22.

Embodiment 35—6-(2-fluorobenzyloxy)-2-(hydroxymethyl)-2-methyl-1-oxaspiro[4.4]nonane The desired product was prepared from 2-(2-fluorobenzyloxy)-1-(3-methyl-3-butenyl)cyclopentanol (Embodiment 25) following procedures similar to those described in Embodiment 23.

Embodiment 36—6-(2-Fluorobenzyloxy)-2-methyl-2-ethyl-1-oxaspiro[4.5]decane

The desired product was prepared from 2-(2-fluorobenzyloxy)-1-(3-ethyl-3-butenyl)cyclohexanol (Embodiment 19) following procedures similar to those described in Embodiment 22.

Embodiment 37—1-(2-Methylbenzyloxy)-6,6-dimethyl-5-oxaspiro[3.4]octane

The desired product was prepared from 2-(2-methylbenzyloxy)-1-(3-methyl-3-butenyl)cyclobutanol following procedures similar to those described in Embodiments 7, 8, 26, and 30.

The invention includes a method of combatting unwanted plants which comprises applying to the locus an effective amount of a compound of Formula I or II. For application, the compound generally is applied most effectively by formulating it with a suitable inert carrier or surface-active agent, or both. The invention therefore, also includes compositions suitable for combatting unwanted plants, such compositions comprising an inert carrier or surface-active agent, or both, and as active ingredient at least one compound of Formula I or II.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone, isophorone, and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3-10% by weight of a dispersing agent, 15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The composition of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I or II, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I or II will be satisfactory.

EXAMPLES OF ACTIVITY WITH RESPECT TO PLANTS

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf *Abutilon theophrasti*
Garden cress—*Lepidium sativum*
Johnsongrass—*Sorghum halepense*
Mustard—*Brassica kaber*
Grain sorghum—*Sorghum vulgare* (Pioneer 265)
Corn—*Zea maize* (deKalb X363)
Cotton—*Gossypium hirsutum* (Acala SJ-2)
Soybean—*Glycine max* (Amsoy 71)
Wheat—*Triticum aestivum* (Cajeme 71)
Sugar beet—*Beta vulgaris*
Cocklebur—*Xanthium pennsylvanicum*

PRIMARY TESTS—PREEMERGENCE ACTIVITY

The preemergence (soil) activity of compounds of the invention was evaluated by planting seeds of barnyardgrass, garden cress, downy brome, velvetleaf, yellow foxtail, and sicklepod in test tubes, nominally measuring 25×200 mm, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 mg of the test compound per each tube containing the seeds of the other plants. The dosages were approximately 22 and 2.2 lb of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

PRIMARY TESTS—POSTEMERGENCE ACTIVITY

The postemergence (foliar) activity of compounds of the invention was evaluated by spraying 10-day-old large crabgrass plants, 13-day-old redroot pigweed plants, 6-day-old Johnsongrass plants, 9-day-old velvetleaf plants, 9-day-old yelloe foxtail plants and 9-day-old sicklepod plants to runoff with a liquid formulation of the test compound. The crabgrass and pigweed plants were sprayed with 2.4 ml of a 0.25% solution (about 10 lb of the test compound per acre), and other plants were sprayed with 2.4 ml of a 0.025% solution (about 1 lb of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence activity tests conducted on the compounds of the invention are set forth in Table 1.

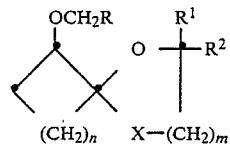

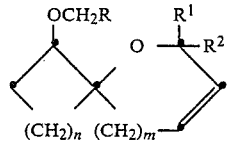

wherein R is an unsaturated group containing up to 4 carbon atoms, a cycloalkyl group containing 3 to 10 carbon atoms, a secondary alkyl group containing 3 to 10 carbon atoms, a phenyl group optionally substituted by 1 or 2 chlorine or fluorine atoms or methyl groups or a 2-pyridinyl group; in formula I, m is 0, 1 or 2; n is 1, 2 or 3; $R^1$ and $R^2$ each independently is a hydrogen atom, an alkyl group containing 1 to 6 carbon atoms, or a hydroxyalkyl group or an alkoxymethyl group in which the alkyl portion contains 1 to 6 carbon atoms; X is $CH_2$ when m is 0, 1 or 2 or X is oxygen when m is 1 or 2; or in formula II, n is 1, 2 or 3; m is 0 or 1; and $R^1$ and $R^2$ each independently is a hydrogen atom, an alkyl group containing 1 to 6 carbon atoms, or a hydroxyalkyl or an alkoxymethyl group in which the alkyl portion contains 1 to 6 carbon atoms.

2. A compound according to claim 1 wherein $R^1$ and $R^2$ each independently is a hydrogen atom or a methyl or an ethyl group.

3. A compound according to claim 2 wherein $R^1$ and $R^2$ each is a methyl group.

4. A compound according to claim 2 wherein R is an ethynyl group, a 2-pyridinyl group or a phenyl group optionally substituted by 1 or 2 chlorine or fluorine atoms or methyl groups.

5. A compound according to claim 4 wherein R is a 2-chlorophenyl, a 2-fluorophenyl or a 2-methylphenyl group.

6. A compound according to claim 5 wherein m is 1 in formula I or m is 0 in formula II.

7. A compound according to claim 6 wherein n is 1.

8. A compound according to claim 6 of formula I in which X is $CH_2$.

TABLE 1

| | HERBICIDAL ACTIVITY | | | | | | | | | | | |
|---|---|---|---|---|---|---|---|---|---|---|---|---|
| | Preemergence (Soil) | | | | | | Postemergence (Foliar) | | | | | |
| Embodiment | Barnyard Grass | Garden Cress | Downy Brome | Velvet Leaf | Yellow Foxtail | Sicklepod | Crab Grass | Pig Weed | Johnson Grass | Velvet Leaf | Yellow Foxtail | Sicklepod |
| 3 | 9 | 6 | 7 | 4 | 7 | 3 | 2 | 2 | 0 | 0 | 0 | 0 |
| 12 | 9 | 7 | 6 | 3 | 6 | 2 | 3 | 3 | 0 | 2 | 0 | 0 |
| 20 | 6 | 3 | 3 | 0 | 3 | 0 | 3 | 4 | 0 | 0 | 0 | 0 |
| 21 | 8 | 7 | 2 | 1 | 3 | 2 | 3 | 3 | 0 | 0 | 0 | 0 |
| 22 | 9 | 6 | 7 | 3 | 6 | 4 | 4 | 4 | 2 | 2 | 1 | 1 |
| 23 | 8 | 5 | 3 | 0 | 0 | 0 | 2 | 4 | 1 | 2 | 0 | 2 |
| 6 | 9 | 7 | 7 | 4 | 5 | 4 | 0 | 2 | 1 | 0 | 1 | 0 |
| 15 | 9 | 7 | 8 | 6 | 8 | 6 | 7 | 3 | 1 | 2 | 2 | 2 |
| 34 | 9 | 5 | 6 | 3 | 6 | 3 | 5 | 3 | 1 | 2 | 0 | 2 |
| 35 | 6 | 4 | 0 | 0 | 0 | 0 | 2 | 3 | 1 | 3 | 0 | — |
| 29 | 9 | 6 | 7 | 2 | 6 | 3 | 0 | 0 | 0 | 0 | 0 | 0 |
| 9 | 9 | 6 | 6 | 3 | 3 | 3 | 0 | 0 | 0 | 0 | 0 | 0 |
| 18 | 9 | 7 | 9 | 3 | 8 | 5 | 3 | 3 | 1 | 2 | 0 | 2 |
| 30 | 9 | 7 | 9 | 4 | 8 | 6 | 7 | 2 | 2 | 2 | 2 | 3 |
| 37 | 9 | 7 | 9 | 6 | 7 | 6 | 6 | 2 | 5 | 5 | 7 | 6 |
| 36 | 9 | 2 | 6 | 2 | 6 | 0 | 7 | 2 | 2 | 2 | 7 | 2 |

What is claimed is:

1. A novel compound of formulas I or II

9. A plant growth regulating composition comprising an effective amount of an active ingredient of a compound according to claim 1 and at least one carrier or surface-active agent.

10. A method of regulating plant growth at a locus comprises applying to the locus or the plant an effective amount of an active ingredient of a compound according to claim 1.

11. A method according to claim 9 wherein plant growth is regulated by depressing growth of the plant or by killing the plant.

* * * * *